United States Patent [19]

Mookherjee et al.

[11] Patent Number: 4,536,583

[45] Date of Patent: Aug. 20, 1985

[54] PROCESS FOR PREPARING MIXTURES CONTAINING 8,9-EPITHIO-1-P-MENTHENE

[75] Inventors: Braja D. Mookherjee, Holmdel, N.J.; Bernard J. Chant, Rye, N.Y.; William J. Evers, Locust, N.J.; Richard A. Wilson, Westfield, N.J.; Michael J. Zampino, North Bergen, N.J.; Manfred H. Vock, Locust, N.J.

[73] Assignee: International Flavors & Fragrances Inc., New York, N.Y.

[21] Appl. No.: 519,371

[22] Filed: Aug. 1, 1983

[51] Int. Cl.³ .................... C07D 331/02; A61K 7/46
[52] U.S. Cl. .................................. 549/1; 252/522 R
[58] Field of Search ...................... 252/522 R; 549/1

[56] References Cited

U.S. PATENT DOCUMENTS

| | | | |
|---|---|---|---|
| 3,505,432 | 4/1970 | Neuwald | 260/93.7 |
| 3,632,396 | 1/1972 | Peres-Zamora | 252/8.6 |
| 3,886,289 | 5/1975 | Sanders et al. | 426/65 |
| 3,959,508 | 5/1976 | Pittet et al. | 252/522 R |
| 4,028,279 | 6/1977 | Van Ouwerkerk et al. | 252/522 R |
| 4,058,472 | 11/1977 | Kablaoui | 252/558 |
| 4,058,490 | 11/1977 | Prince | 252/554 |
| 4,067,910 | 1/1978 | Frater et al. | 252/522 R |
| 4,211,242 | 7/1980 | Mookherjee et al. | 252/522 R |
| 4,247,498 | 1/1981 | Castro | 264/41 |
| 4,334,098 | 6/1982 | Mookherjee et al. | 252/522 R |
| 4,478,865 | 10/1984 | Demole et al. | 426/535 |

FOREIGN PATENT DOCUMENTS

| | | |
|---|---|---|
| 0054847 | 6/1982 | European Pat. Off. |
| 2615393 | 10/1976 | Fed. Rep. of Germany |
| 520479 | 3/1972 | Switzerland |
| 465662 | 5/1937 | United Kingdom ............... 549/1 |

OTHER PUBLICATIONS

Snyder et al., "J.A.C.S.", vol. 69, (1947), pp. 2672–2674.
Demole et al., "Helvetica Chimica Acta", vol. 65, (1982), pp. 1785–1792.
Arctander, "Perfume & Flavor Chemicals", vol. II, (1969), #2513.
Rupe et al., "Helv. Chimica Acta", vol. 18, (1935), pp. 535–542.
Starks et al., "Phase Transfer Catalysis", (1978), pp. 344–345.

Primary Examiner—Anton H. Sutto
Attorney, Agent, or Firm—Arthur L. Liberman

[57] ABSTRACT

Described is a process for preparing a mixture of t-mercapto terpenes defined according to the structure:

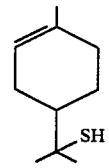

and α-terpineol defined according to the structure:

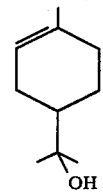

including the step of reacting the compound defined according to the structure:

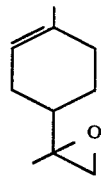

with an alkali metal thiocyanate defined according to the structure:

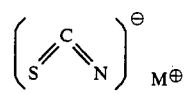

wherein M represents alkali metal such as sodium, potassium or lithium in the presence of a phase transfer catalyst. The resulting product is then treated with lithium aluminum hydride followed by aqueous mineral acid to form a mixture of α-terpineol and the compound defined according to the structure:

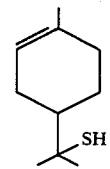

which mixture is useful for its organoleptic properties.

1 Claim, 4 Drawing Figures

GLC PROFILE FOR EXAMPLE II.

GLC PROFILE FOR EXAMPLE I.

PROCESS FOR PREPARING MIXTURES CONTAINING 8,9-EPITHIO-1-P-MENTHENE

BACKGROUND OF THE INVENTION

Our invention relates to mixtures of one or more t-mercapto terpene isomers defined according to the structure:

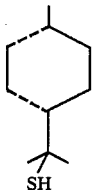

wherein one of the dashed lines represents a carbon-carbon double bond and the other of the dashed lines represents a carbon-carbon single bond taken further together with α-terpineol, β-phenylethyl alcohol, 3-methyl-1-phenyl-pentanol-5 and/or butanoyl cyclohexane derivatives as well as organoleptic uses thereof and processes for preparing such mixtures including the novel process of reacting the epoxide defined according to the structure:

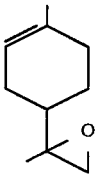

with an alkali metal thiocyanate in order to form the compound having the structure:

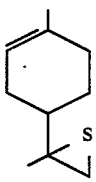

and then reducing the compound having the structure:

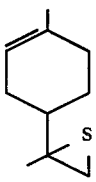

with lithium aluminum hydride followed by treatment with aqueous mineral acid to form a compound having the structure:

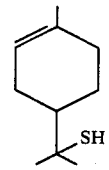

Chemical compounds which can provide natural rose petal, green, iris and hyacinth aroma profiles are highly desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

By the same token, materials which can provide guava-like, grapefruit-like, black current-like, tomato leaf and passion fruit aroma and taste nuances are highly desirable in the art of application of flavors of foodstuffs, toothpastes, chewing gums, medicinal products and chewing tobaccos. Many of the natural materials which provide such flavor nuances are high in cost, vary in quality from one batch to another and/or are generally subject to the usual variations of natural products. such flavor nuances, furthermore, are highly useful in flavoring tobacco, guava, grapefruit, tropical fruit, raspberry, strawberry and passion fruit-flavored foodstuffs.

Artificial flavoring agents for foodstuffs have received increasing attention in recent years. For many years such food flavoring agents have been preferred over natural flavoring agents at least in part due to their diminished cost and their reproducible flavor qualities. For example, natural food flavoring agents such as extracts, concentrates and the like are often subject to wide variations due to changes in quality, type and treatment of the raw materials. Such variations can be reflected in the end product and result in unfavorable flavor characteristics in said end product. Additionally, the presence of the natural product in the ultimate food may be undesirable because of increased tendency to spoil. This is particularly troublesome in food and food uses where such products as dips, soups, chips, sausages, gravies and dairy dessert products and the like are apt to be stored prior to use.

The fundamental problem in creating artificial flavor agents is that the artificial flavor to be achieved be as natural as possible. This generally proves to be a difficult task since the mechanism for flavor development in many foods, medicinal products, chewing gums, toothpastes and chewing tobaccos is not completely known. This is noticeable in products having tomato, guava, grapefruit, tropical fruit-like, raspberry, strawberry and passion fruit flavor characteristics.

Even more desirable are products that can serve to substitute for difficult to obtain natural perfumery oils and at the same time substitute for natural flavoring ingredients in foodstuffs, chewing gums, medicinal products, toothpastes and chewing tobaccos.

The compound having the structure:

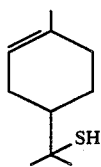

is a known ingredient in grapefruit aroma and taste. The compound having the structure:

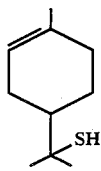

occurs naturally in grapefruit aromas as disclosed by Demole, Enggist and Ohloff, Helvetica Chimica Acta, Vol. 65, Fasc. 6, (1982), Number 176 at page 1784 (title: 1-p-Menthene-8-thiol: A Powerful Flavor Impact Constituent of Grapefruit Juice (Citrus Paradisi MacFayden)).

The compound having the structure:

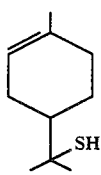

as well as its individual isomers having the structures:

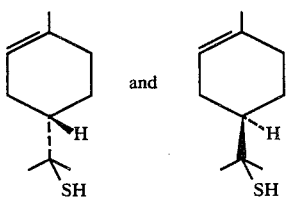

is also disclosed and claimed for its use in augmenting or enhancing the aroma or taste of grapefruit flavored foodstuffs in published European Patent Application No. 54,847 published on June 30, 1982 relying on a priority date of Dec. 23, 1980 (Swiss Patent Application No. 9513/80) assigned to Firmenich S. A. of Geneva, Switzerland. The said published European Application No. 54,847 also discloses and claims the use of the compounds having the structures:

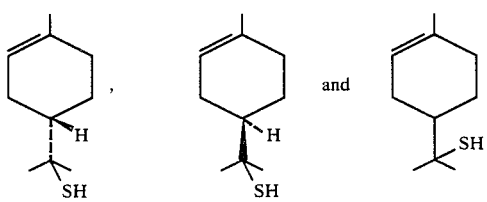

in augmenting or enhancing the aroma of perfume compositions and perfumed articles.

Nothing in published European Patent Application No. 54,847 discloses the unexpected, unobvious and advantageous results when using mixtures of such t-mercapto terpenes as those having the structures:

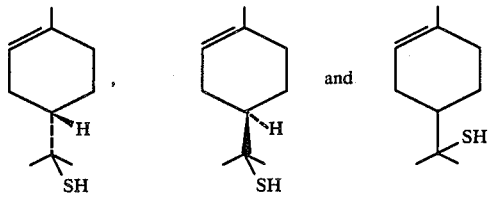

in admixture with α-terpineol having the structure:

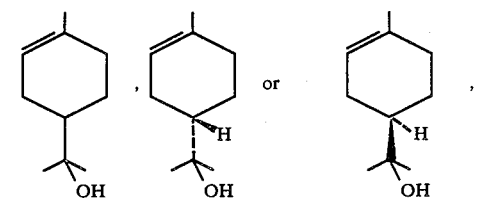

β-phenylethyl alcohol, 3-methyl-1-phenyl-pentanol-5 and/or butanoyl cyclohexane derivatives defined according to the generic structure:

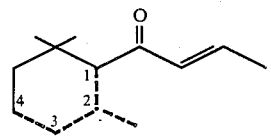

wherein the dashed lines are as defined above.

The individual components of our novel mixture are known in the art of perfumery and a number of them are also known individually in augmenting or enhancing the aroma or taste of foodstuffs, chewing gums, toothpastes and medicinal products.

Thus, β-phenylethyl alcohol defined according to the structure:

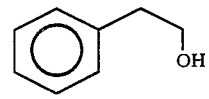

is indicated by Arctander "Perfume and Flavor Chemicals(Aroma Chemicals)" published 1969, Volume II at Monograph 2513 to have a mild and warm, rose, honey-like odor of moderate to poor tenacity. Arctander further indicates that phenylethyl alcohol in its poorer grades shows earthy, pungent, more hyacinth-like topnotes or greener "gassy" notes. At Monograph 2513, Arctander also indicates that β-phenylethyl alcohol finds some use in flavor compositions, mainly in imitation butter, strawberry, raspberry ("very common ingredient"), caramel, honey, melon and in various fruit complexes. Arctander indicates that the concentration of phenylethyl alcohol used is from about 0.1 up to about 20 ppm.

The compound having the structure:

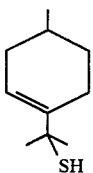

is indicated to be useful in perfumery in published German Offenlegungsschrift No. 26 15 393 published on Oct. 21, 1976. The German Offenlegungsschrift corresponds to U.S. Pat. No. 4,067,910 issued on Jan. 10, 1978. Such compounds are also indicated to be useful for augmenting or enhancing the aroma or taste of foodstuffs.

U.S. Pat. No. 4,217,253 issued on Aug. 12, 1980 discloses mixtures of 3-methyl-1-phenyl-pentanol-5 having the structure:

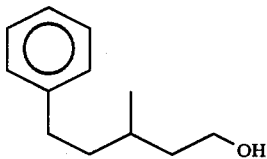

and one or more butanoyl cyclohexane derivatives defined according to the structure:

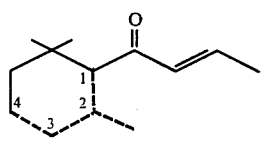

wherein one of the dashed lines is a carbon-carbon double bond or two of the dashed lines are carbon-carbon double bonds but that when two of the dashed lines each represent a carbon-carbon double bond, then the carbon-carbon double bonds are conjugated. Examples of the butanoyl cyclohexane derivatives of U.S. Pat. No. 4,217,253 are those having the structure:

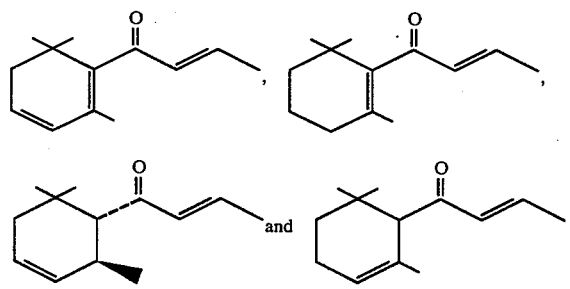

(wherein the dashed line in the structure:

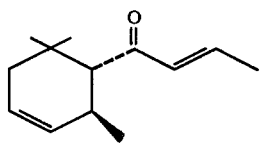

represents a configuration of the butanoyl moiety "trans" with respect to the methyl moiety at the "2" position on the cyclohexene ring). It is disclosed in said U.S. Pat. No. 4,217,253 that perfume compositions and perfumes having extended long-lasting, highly intense and natural-like rosey notes and perfumed articles having extended, long-lasting, highly intense rosey aromas with woody, green and earthy notes may be provided by the utilization of mixtures of (i) one or more butanoyl cyclohexane derivatives defined according to the structure:

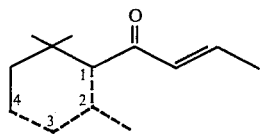

wherein one or two of the dashed lines is a carbon-carbon double bond and the other of the dashed lines are carbon-carbon single bonds with the proviso that if two of the dashed lines are carbon-carbon double bonds, the carbon-carbon double bonds are conjugated and (ii) 3-methyl-1-phenyl-pentanol-5 racemic mixtures or individual stereoisomers having one of the structures:

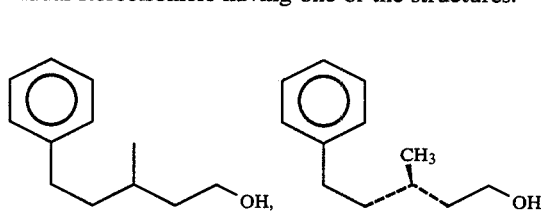

or

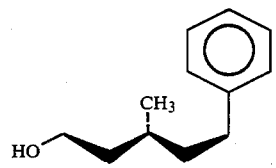

In U.S. Pat. No. 4,217,253 it is indicated that organoleptic properties obtained when using the combination of mixtures of 3-methyl-1-phenyl-pentanol-5 and one or more butanoyl cyclohexane derivatives as defined supra is more than merely additive of the individual organoleptic properties of the 3-methyl-1-phenyl-pentanol-5 compound taken alone or in combination and the butanoyl cyclohexane derivatives (taken alone or in combination with one another) and that the effect is synergistic. The synergism existent as a result of practicing our invention, however, is unexpected, unobvious and advantageous notwithstanding the synergism described and taught in U.S. Pat. No. 4,217,253.

U.S. Pat. No. 4,028,279 entitled "Novel Fragrance Compositions Containing 2,6,6-Trimethyl-1-Cyclohexene-1-yl Acetaldehyde and Phenyl $C_6$ Ketone" relates to mixtures of (i) either or both of the phenyl $C_6$ ketones, 2,5-dimethyl-5-phenylhexanone-4 and 2,5-dimethyl-5-phenylhexen-1-one and (ii) 2,2,6-trimethyl-1-cyclohexen-1-yl acetaldehyde used to alter, modify, enhance or impart aromas in or to perfumes, perfume compositions and/or perfumed articles. It is disclosed in said U.S. Pat. No. 4,028,279 that such perfume compositions containing such mixtures have intense rosey aromas with woody, green and earthy notes. The structure of the phenyl $C_6$ ketones disclosed in U.S. Pat. No. 4,028,279 is:

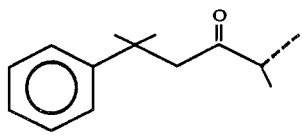

The structure of the betacyclohomocitral used in U.S. Pat. No. 4,028,279 is:

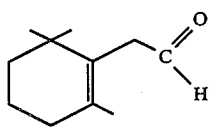

wherein the dashed line may be either a carbon-carbon single bond or a carbon-carbon double bond.

In U.S. Pat. No. 3,595,508 issued on May 25, 1976, mixtures of (i) 2,2,6-trimethyl-1-cyclohexen-1-yl acetaldehyde and (ii) 2,6,6-trimethyl crotonyl-1,3-cyclohexadiene having the structure:

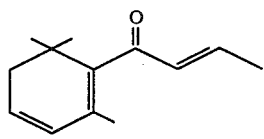

are indicated to produce in perfumes, rosey, woody, camphoraceous, green and earth notes.

Nothing in the prior art teachings imply or state that such mixtures as are disclosed and claimed in the instant case can be used to enhance and extend specific rose nuances of such materials as β-phenylethyl alcohol, α-terpineol, butanoyl cyclohexane derivatives having the generic structure:

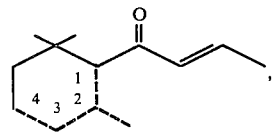

and 3-methyl-1-phenyl-pentanol-5 using one or both of the t-mercapto terpene derivatives defined according to the structures:

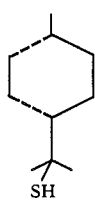

wherein one of the dashed lines is a carbon-carbon double bond and the other of the dashed lines is a carbon-carbon single bond.

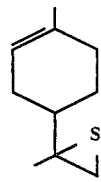

(conditions: Carbowax column programmed at 120°–210° C. at 8° C. per minute).

Figure 2:
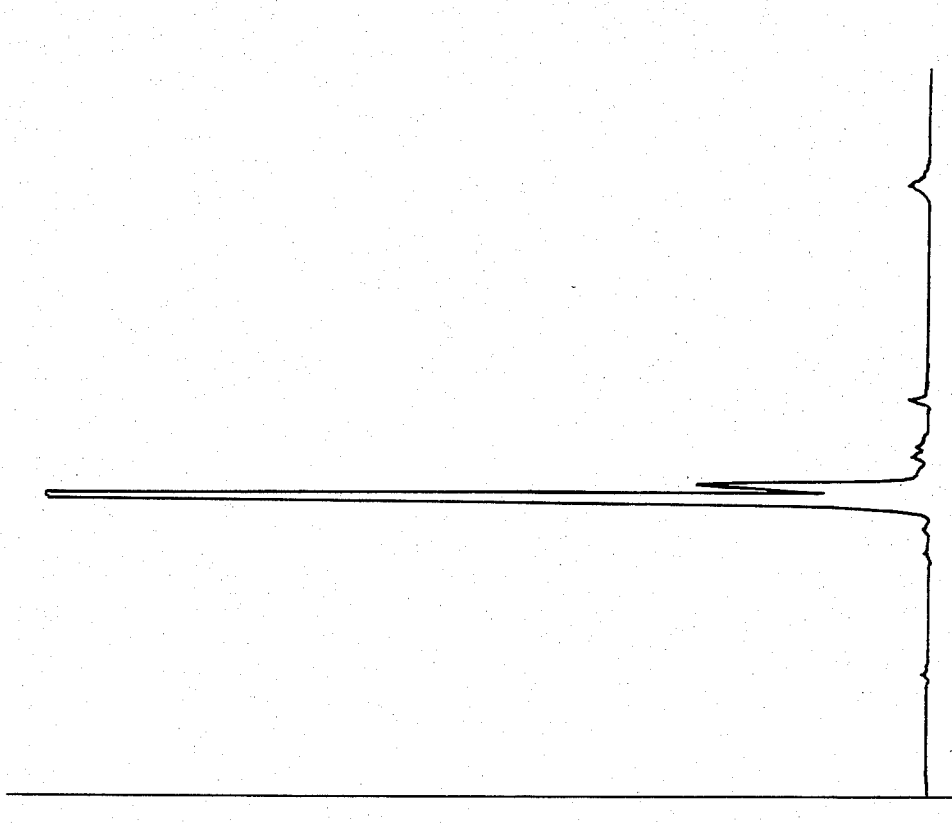

FIG. 2 is the GLC profile for the distillation product of the reaction product of Example II containing the compounds having the structures:

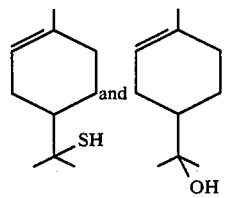

with 82% of the product being the compound having the structure:

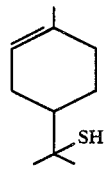

and 18% of the product being the compound having the structure:

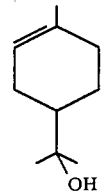

Figure 3:
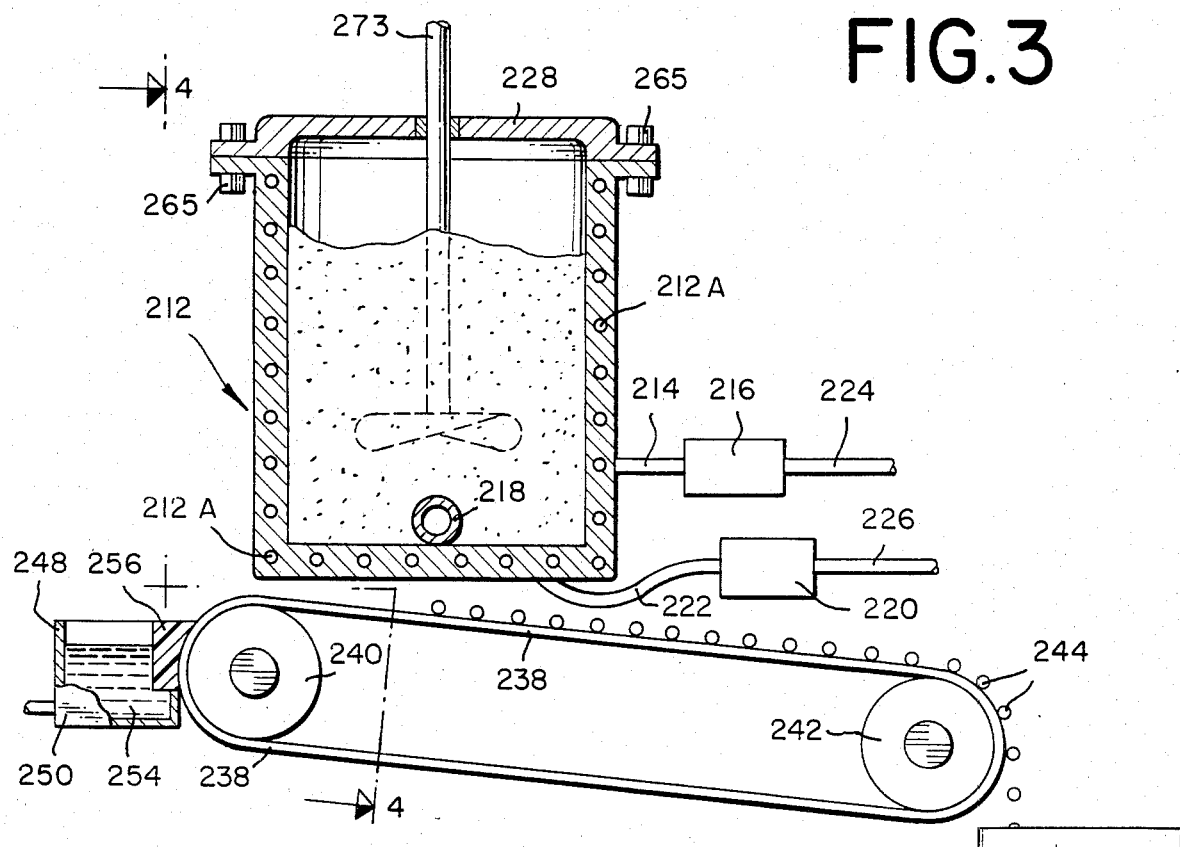

FIG. 3 is a partial side elevation and partial sectional view of an apparatus for forming scented polymer using a mixture of compounds having the structures:

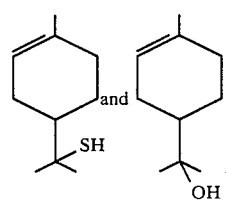

produced according to Example II.

Figure 4:
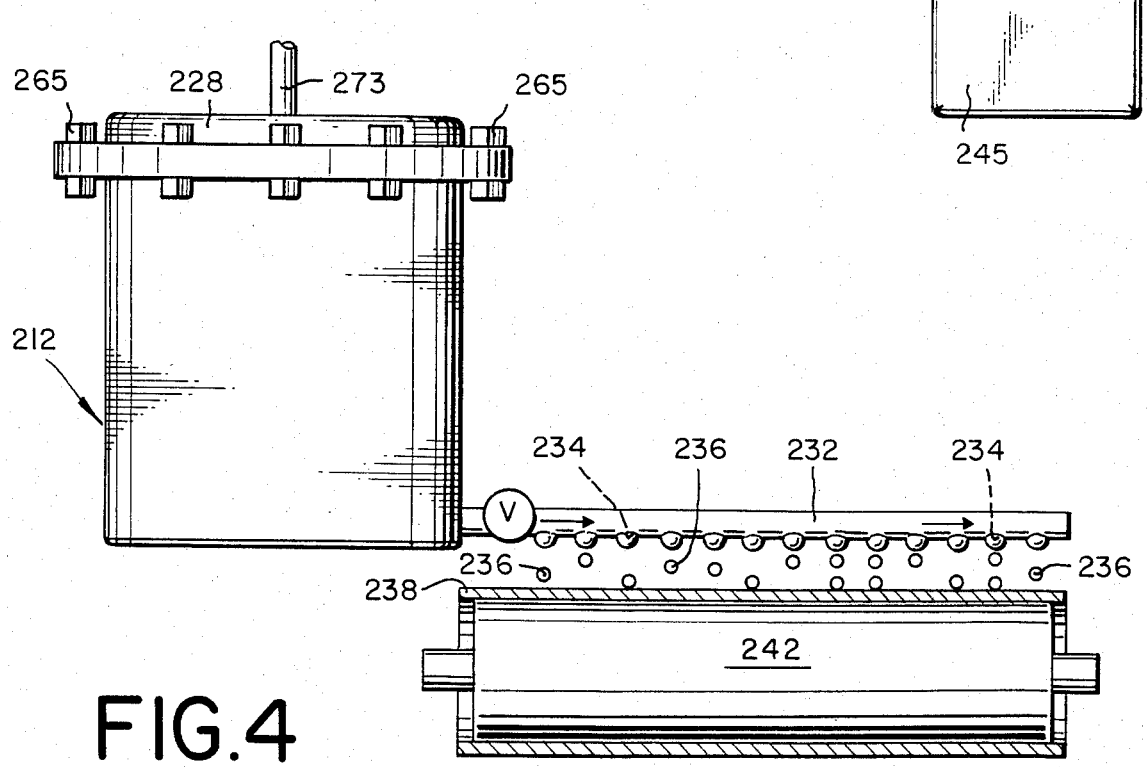

FIG. 4 is a section taken on line 4—4 of FIG. 3.

DETAILED DESCRIPTION OF THE DRAWINGS

Figure 1:
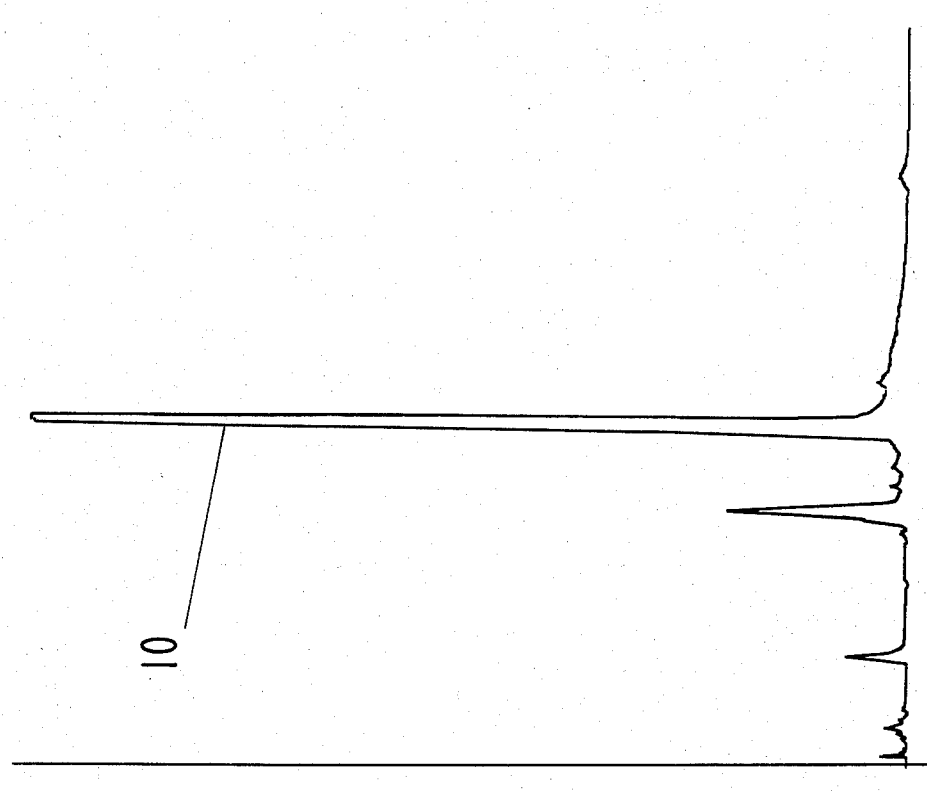
FIG. 1 is the GLC profile for the reaction product of Example I containing the compound having the structure.

FIG. 1 is the GLC profile for the reaction product of Example I. The peak indicated by reference numeral "10" on the GLC profile is the peak for the compound having the structure:

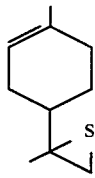

Referring to the drawings in FIGS. 3 and 4 in particular, the invention embodied therein comprises a device for forming scented polymer pellets (e.g. polyethylene, polypropylene or mixtures of polyepsilon caprolactone and polyethylene or polypropylene or co-polymers of polyvinyl acetate and polyethylene) which comprises a vat or container 210 into which a mixture of polymer such as polyethylene and a mixture of compounds defined according to the structures:

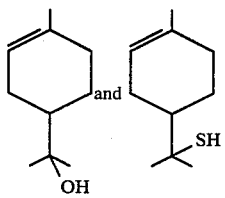

for example, or a mixture of perfume materials including as a key ingredient one of the isomers defined according to the structure:

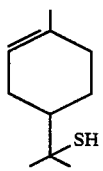

taken further together with β-phenylethyl alcohol having the structure:

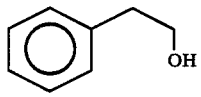

or a mixture of perfume materials including as a key ingredient one of the isomers defined according to the structure:

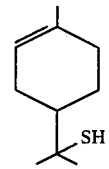

as well as the compound having the structure:

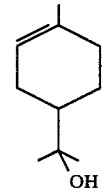

as well as β-phenylethyl alcohol having the structure:

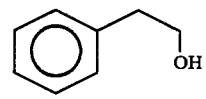

for example, is placed.

The container is closed by an air-tight lid 228 clamped to the container by clamps 265. A stirrer 273 traverses the lid or cover 228 in air-tight manner and is rotated in suitable manner. A surrounding cylinder 212 having heating coils which are supplied with electrical current through cable 214 from a rheostat or control 216 is operated to maintain the temperature inside the container 210 such that the polymer such as polyethylene in the container will be maintained in a molten or liquid state. It has been found advantageous to employ a colorless, odorless polymer such as low density polyethylene with a viscosity ranging between 180 and 220 centistokes and having a melting point in the neighborhood of 220° F. The heater 212 is operated to maintain the upper portion of the container 210 within a temperature range of from 250°–350° F. An additional bottom heater 218 is regulated through a control 220 connected thereto through a connecting wire 222 to maintain the lower portion of the container 210 within a temperature range of from 250° to 350° F.

In accordance with this aspect of the invention, a polymer such as polyethylene or polypropylene is added to the container 210 and is then heated from 10 to 12 hours whereafter a scent or aroma-imparting material containing a mixture of compounds having the structures:

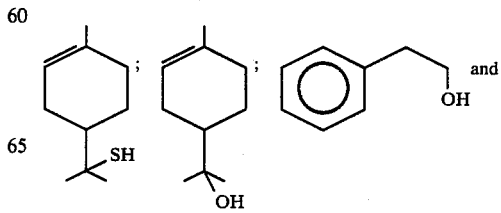

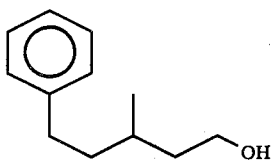

is quickly added to the melt. The material must be compatible with the polymer and forms a homogeneous liquid melt therewith. The heat resisting material, generally about 10–40% by weight of the above mixture, is added to the polymer.

After the above mixture of perfumery chemicals is added to container 210, the mixture is stirred for a few minutes, for example 5 to 15 minutes, and maintained within the temperature range as indicated previously by the heating coils 212 and 218 respectively. The controls 216 and 220 are connected through cables 224 and 226 to a suitable supply of electric current for supplying the power for heating purposes.

Thereafter the valve "V" is opened permitting the mass to flow outwardly through a conduit 232 having a multiplicity of orifices 234 adjacent the lower side thereof. The outer end of the conduit 232 is closed so that the liquid polymer and perfumery chemical mixture will continuously drop through the orifice 234 downwardly from the conduit 232. During this time the temperature of the polymer and the perfumery chemical mixture in the container 210 is accurately controlled so that a temperature in the range of from 210° F. up to 275° F. will exit in the conduit 232. The regulation of the temperature through the control 216 and the control 220 is essential in order to insure temperature balance to provide for the continuous dropping or dripping of molten polymer and perfumery chemical mixture of our invention through the orifices 234 at a range which will insure the formation of droplets 236 which will fall downwardly onto a moving conveyor belt 238 trained to run between conveyor wheels 240 and 242 beneath the conduit 232. When the droplets 236 fall onto the conveyor belt 238 they form pellets 244 which harden almost instantaneously and fall off the end of the conveyor 238 into a container 246 which is advantageously filled with water or some other suitable liquid to insure the rapid cooling of each of the pellets. The pellets 244 are then collected from the container 246 and packaged for shipment.

A feature of the invention is the provision for moistening the conveyor belt 238 to insure the rapid formation of the solid polymer scented pellets 244 witnhout sticking to the belt. The belt 238 is advantageously of a material which will not normally stick to a melted polymer but the moistening means 248 insures a sufficiently cold temperature of the belt surface for the adequate formation of the pellets 244. The moistening means comprises a container 250 which is continuously fed with water 252 to maintain a level 254 for moistening a sponge element 256 which bears against the exterior surface of the belt 238.

THE INVENTION

It has now been discovered that novel perfume compositions and perfumes as well as perfumed articles having extended long-lasting, highly intense and natural-like rose petal, green, iris and hyacinth notes may be provided by the utilization of mixtures of:

(i) one or more t-mercapto terpene isomers defined according to the structure:

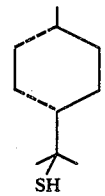

wherein one of the dashed lines represents a carbon-carbon double bond and the other of the dashed lines represents a carbon-carbon single bond; and (ii) one or more of α-terpineol having the structure:

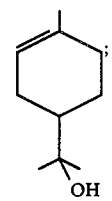

and/or β-phenylethyl alcohol having the structure:

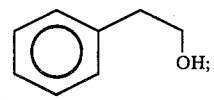

and/or 3-methyl-1-phenyl-pentanol-5 having the structure:

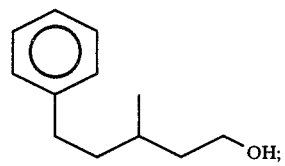

and/or one or more butanoyl cyclohexane derivatives defined according to the structure:

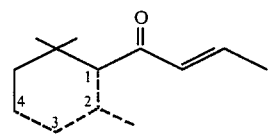

wherein one or two of the dashed lines is a carbon-carbon double bond and the other of the dashed lines are carbon-carbon single bonds with the proviso that if two of the dashed lines are carbon-carbon double bonds, the carbon-carbon double bonds are conjugated.

It has been further discovered that novel foodstuff, chewing gum, toothpaste, medicinal product and chewing tobacco flavors having raspberry/guava-like, grapefruit-like, black current-like, tomato leaf-like and passion fruit-like flavor and aroma nuances may be provided by the use of mixtures of:

(i) one or more t-mercapto terpenes defined according to the structure:

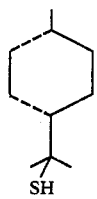

wherein one of the dashed lines is a carbon-carbon double bond and the other of the dashed lines is a carbon-carbon single bond; and (ii) α-terpineol having the structure:

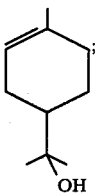

and/or β-phenylethyl alcohol having the structure:

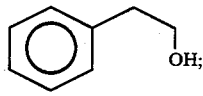

and/or 3-methyl-1-phenyl-pentanol-5 having the structure:

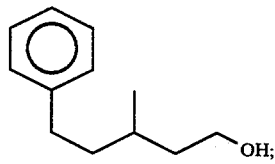

and/or one or more butanoyl cyclohexane derivatives defined according to the structure:

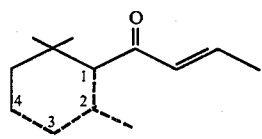

wherein one or two of the dashed lines is a carbon-carbon double bond and the other of the dashed lines are carbon-carbon single bonds with the proviso that if two of the dashed lines are carbon-carbon double bonds, the carbon-carbon double bonds are conjugated.

With reference to the 3-methyl-1-phenyl-pentanol-5 useful in our invention, a racemic mixture of such compound may be used defined according to the structure:

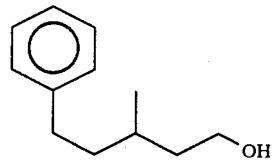

or one of the isomers of such compound may be used which isomers have the structures:

 and 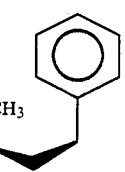

With respect to the butanoyl cyclohexane derivatives useful in our invention, one of the following butanoyl cyclohexane compounds may be used having one of the following structures:

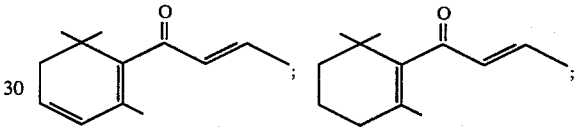

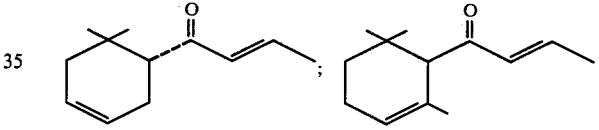

wherein in the compound having the structure:

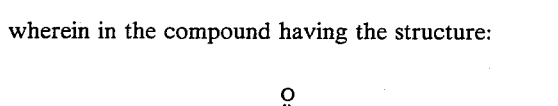

the dashed line represents a configuration of the butanoyl moiety "trans" with respect to the methyl moiety at the "2" position on the cyclohexane ring.

With respect to the t-mercapto terpene compounds of our invention defined according to the structure:

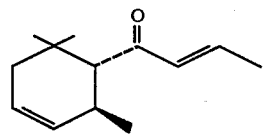

wherein one of the dashed lines is a carbon-carbon double bond and the other of the dashed lines is a carbon-carbon single bond, the compounds contemplated for use in conjunction with our invention are defined according to the structures:

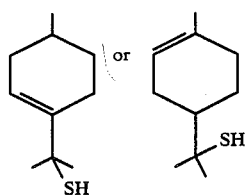

(representing a racemic mixture); or isomers thereof having the structures:

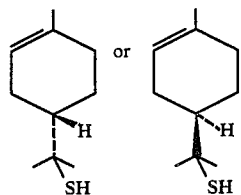

Hereinafter the mixture of t-mercapto terpenes and the α-terpineol and/or β-phenylethyl alcohol and/or 3-methyl-1-phenyl-pentanol-5 and/or butanoyl cyclohexane derivatives will be referred to as the mercapto terpene-oxohydrocarbon mixture. The t-mercapto terpenes having the structure:

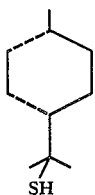

used in our invention will hereinafter be referred to as "t-mercapto terpenes". The α-terpineol and/or β-phenylethyl alcohol and/or 3-methyl-1-phenyl-pentanol-5 or butanoyl cyclohexane derivatives of our invention will be referred to as "oxohydrocarbons" as a group.

The 3-methyl-1-phenyl-pentanol-5 described as having one of the structures:

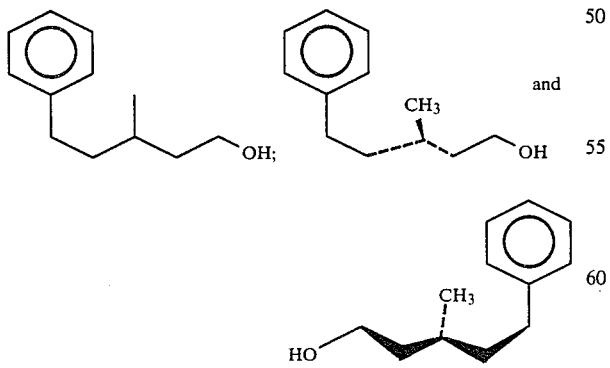

may be prepared according to the procedure described by Rupe Hirschmann and Werdenberg at Helv. Chimica Acta. 18 (1935) pages 535–542 (abstracted at Beilstein E III 6, 1997, H6,551).

Methods for preparing the butanoyl cyclohexane derivatives used in our invention are described in Swiss Pat. No. 520,479 issued on May 12, 1972 as well as application for United States Letters Patent Ser. No. 851,727 filed on Nov. 15, 1977, now U.S. Pat. No. 4,211,242 issued on July 8, 1980 and U.S. Pat. No. 4,334,098 issued on June 8, 1982.

Contemplated within the scope of our invention are weight ratios of t-mercapto terpene derivative having the generic structure:

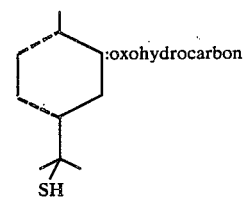

of from about $1 \times 10^{-7}:1$ up to about $1:0.1$.

When our invention is practiced in the foodstuff, chewing gum, medicinal product and toothpaste flavor area, the mole ratio of mercapto terpene:oxohydrocarbon (other than α-terpineol) is from about $1 \times 10^{-7}:1$ down to about $1 \times 10^{-4}:1$.

When practicing our invention with respect to perfumery and perfumed articles, the ratio of t-mercapto terpene:oxohydrocarbon (other than α-terpineol) may vary from about $1 \times 10^{-7}$ up to about $1 \times 10^{-3}$ with a preferred ratio of $1 \times 10^{-6}$ up to $5 \times 10^{-6}$.

α-terpineol is a side product in the formation of the compounds having the structure:

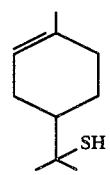

and the mole ratio of α-terpineol to compound having the structure:

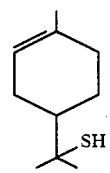

may vary from 1:0.1 down to 0.1:1.

Specifically referring to the unique process of our invention wherein mixtures of α-terpineol and t-mercapto terpene having the structure:

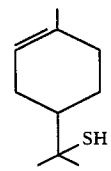

are produced in mole ratios of from 0.8 up to 0.9:0.1 up to 0.2. The novel part of this reaction sequence lies in the reaction of the α-terpineol epoxide having the structure:

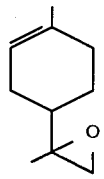

with an alkali metal thiocyanate having the structure:

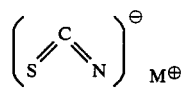

wherein M represents alkali metal such as sodium, potassium and lithium in accordance with the reaction sequence:

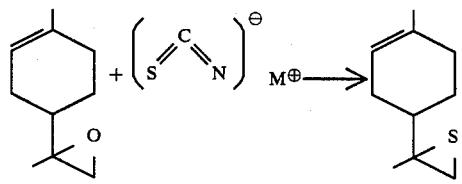

The resulting compound having the structure:

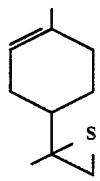

is then reduced with lithium aluminum hydride to form a lithium salt which, in turn, is hydrolyzed in the presence of dilute aqueous mineral acid to form the desired compound of our invention having the structure:

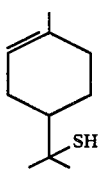

in admixture with α-terpineol having the structure:

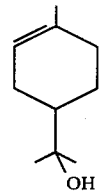

in the ratios as above stated. The second reaction is as follows:

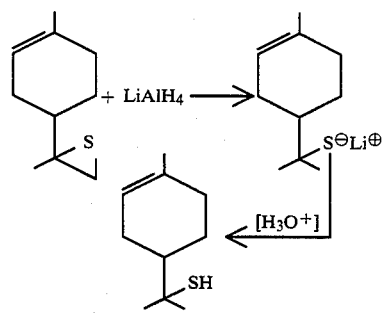

In the prior art, however, a much more complicated technique has been used (for example, in European Published Patent Application No. 054,847 assigned to Firmenich SA and published on June 30, 1982) wherein the terpineol epoxide having the structure:

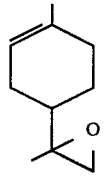

is first reacted with thiourea to form the complex sulfate having the structure:

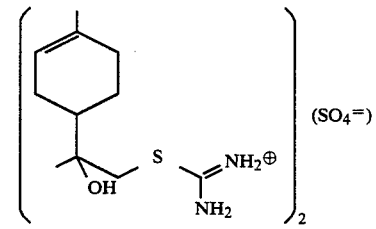

in accordance with the reaction:

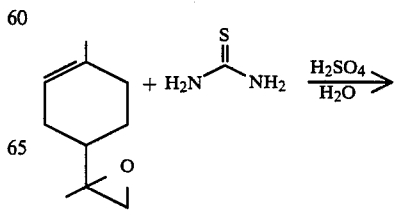

-continued

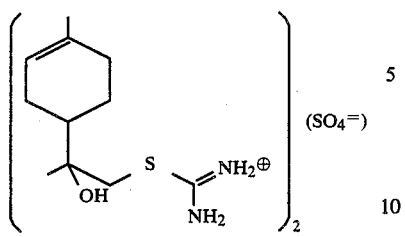

This complex sulfate is then reacted with weak base (e.g. aqueous sodium carbonate) to form the thiirane having the structure:

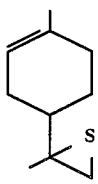

in accordance with the reaction:

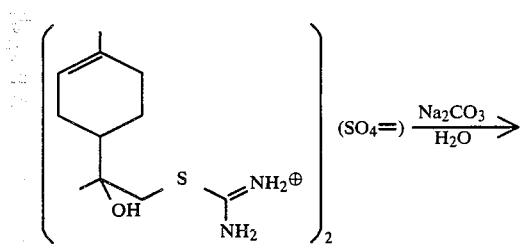

The resulting compound is then reduced in the usual way using lithium aluminum hydride to form the lithium salt followed by hydrolysis using aqueous mineral acid according to the reaction sequence:

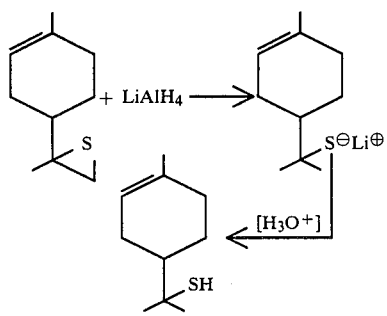

Accordingly, a key aspect of our invention is the use of the unique reaction product of our invention achieved as a result of the reaction of the alkali metal thiocyanate with the terpineol epoxide according to the reaction sequence:

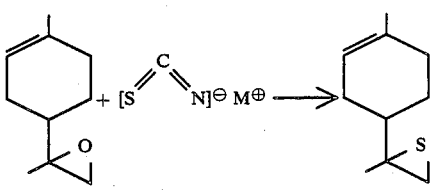

and

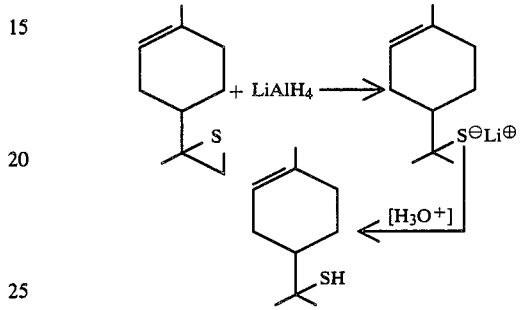

whereby a mixture of compound having the structure:

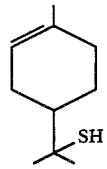

and α-terpineol having the structure:

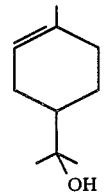

is produced.

When the mixtures of mercapto terpene and one or more of the oxohydrocarbon derivatives of our invention are used as perfume aroma adjuvants, the nature of the co-ingredients included with said mixture of mercapto terpene and one or more of the oxohydrocarbon derivatives in formulating the product composition will also serve to alter the organoleptic characteristics of any ultimate perfumed article treated therewith.

As used herein the terms "alter" and "modify" in their various forms mean supplying or imparting a perfume aroma character or note to be otherwise bland substances or augmenting the existing aroma characteristics where natural aroma is deficient in some regard or supplementing the existing aroma impression to modify its quality, character or aroma.

As used herein the term "enhance" is intended to mean the intensification (without effecting a change in kind or quality of aroma) of one or more aroma nuances and their organoleptic impression of a perfume, perfume composition or one or more perfumed articles.

The mixture of mercapto terpene and one or more oxohydrocarbon derivatives of our invention and one or more auxiliary perfume ingredient including, for example, alcohols other than the β-phenylethyl alcohol or 3-methyl-1-phenylpentanol-5 or α-terpineol of our invention, aldehydes, ketones other than the butanoyl cyclohexane derivatives of the mixture of our invention, nitriles, esters, lactones, natural essential oils, synthetic essential oils and mercaptans other than the mercapto terpenes of our invention, may be admixed so that the combined odors of the individual components produce a pleasant and desired fragrance, particularly and preferably in the rose, iris and hyacinth fragrance area.

It is to be understood that such additional adjuvants are to be organoleptically compatible with each of the mercapto terpenes and oxohydrocarbon derivatives as cited supra of our invention and further that such adjuvants are to be non-reactive under use conditions at room temperature and storage conditions with the mercapto terpenes and oxohydrocarbon derivatives of the mixture of our invention.

Such perfume compositions usually contain (a) the main note or bouquet or foundation stone of the compositions; (b) modifiers which round off and accompany the main note; (c) fixatives which include odorous substances which lend a particular note to the perfume throughout all stages of evaporation and substances which retard evaporation and (d) topnotes which are usually low-boiling, fresh-smelling materials.

It is the individual components which will contribute their particular olfactory characteristics; and these individual components will also alter, modify or enhance the overall effect of the perfume composition. Thus, the mixture of mercapto terpenes and one or more oxohydrocarbon derivatives can be used to alter, augment or enhance the aroma characteristics of a perfume composition, for example, by utilizing or moderating the olfactory reaction contributed by one or more other ingredients in the composition.

The amount of mixture of mercapto terpene and one or more of the oxohydrocarbon derivatives of our invention which will be effective in the perfume composition depends on many factors including the other ingredients, their amounts and the effects which are desired. It has been found that perfume compositions containing as little as $10^{-4}\%$ of the mixture of mercapto terpenes and one or more of the oxohydrocarbon derivatives can be used to impart an interesting natural rose petal, green, iris and hyacinth aroma profile to cosmetics and other products including fabric softener articles used in clothes driers, solid or liquid anionic, cationic, nonionic or zwitterionic detergents and perfumed polymers. The amount employed can range up to 10% of the fragrance components and will depend on considerations of cost, nature of the end product, the effect desired on the finished product and the particular fragrance sought.

The mixture of the mercapto terpenes and one or more oxohydrocarbon derivatives is useful taken alone or in perfume compositions as an olfactory component in anionic, cationic, nonionic or zwitterionic detergents and soaps, space odorants and deodorants, perfumes, colognes, toilet water, bath preparations such as bath oils and bath solids, hair preparations such as lacquers, brilliantines, pomades and shampoos; cosmetic preparations such as creams, deodorants, hand lotions and sun screens; powders such as talcs, dusting powders and face powders; perfumed polymers; insect repellents; animal repellents; and insect and animal pheremones.

When used as an olfactory component, as little as 0.0025% of the mixture of mercapto terpenes and one or more oxohydrocarbon derivatives will suffice to impart a rose petal, green, iris-like and hyacinth-like aroma profile to rose or petitgrain formulations. Generally no more than 3% of the mixture of mercapto terpenes and oxohydrocarbon derivatives based on the ultimate end product is required in the perfumed article. Accordingly, the range of mixture of mercapto terpene and oxohydrocarbon derivative in the perfumed article may vary from about 0.0025% up to about 3% by weight of the perfumed article.

In addition, the perfume composition or fragrance composition of our invention can contain a vehicle or carrier for the mixture of mercapto terpene and hydrocarbon derivatives of our invention. The vehicle can be a liquid such as a non-toxic alcohol (e.g. 95% food grade ethanol), a non-toxic glycol (e.g. propylene glycol) or the like. The carrier can also be an absorbent solid such as a gum (e.g. gum arabic, xanthan gum or guar gum or mixtures of same) or components for encapsulating the composition (such as gelatin as by means of coacervation) or such as a urea formaldehyde prepolymer for formation of the ureaformaldehyde polymer around a liquid perfume center.

More specifically, the mixtures of mercapto terpene and oxohydrocarbon derivatives of our invention may be blended into polymers when forming a perfumed polymer by means of extrusion using a single or double screw extruder or technique such as that set forth in U.S. Pat. No. 4,247,498 issued on Jan. 27, 1981 (the specification for which is incorporated herein by reference) which discloses microporous polymers which are capable of containing volatile substances such as perfumes and the like in forms ranging from films to blocks and intricate shapes from synthetic thermoplastic polymers such as olefinic condensation or oxidation polymers. Other techniques of blending the mixtures of mercapto terpenes and oxohydrocarbon derivatives of our invention with polymers are exemplified in U.S. Pat. No. 3,505,432 (the specification for which is incorporated by reference herein) which discloses a method for scenting a polyolefin with such materials as the mixtures of mercapto terpenes and oxohydrocarbon derivatives of our invention which process comprises:

(a) mixing a first amount of the liquid polyolefin (e.g. polyethylene or polypropylene) with a relatively large amount of scent-imparting material (in this case the mixture of mercapto terpenes and oxohydrocarbon derivatives of our invention) to form a flowable mass;

(b) forming drops of said mass and causing substantially instantaneous solidification of said drops into polyolefin pellets having a relatively large amount of such scent-imparting materials as the mixtures of mercapto terpenes and oxohydrocarbon derivatives of our invention imprisoned therein;

(c) melting said pellets with a second amount of polyolefin with said second amount being larger than said first amount; and (d) solidifying the melt of (c).

As stated supra, a key constituent of the perfume composition or flavor composition of our invention is a mixture of compounds defined according to the structures:

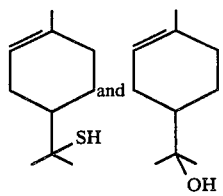

produced by means of a unique process according to the reactions:

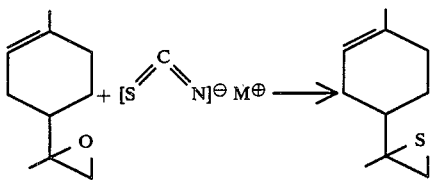

and

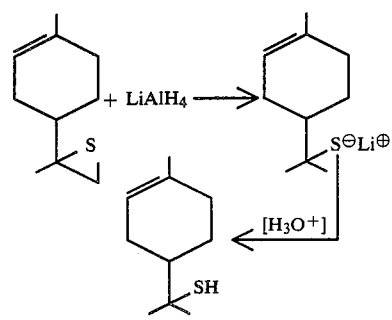

wherein M represents sodium, potassium or lithium. In reacting the limonene epoxide having the structure:

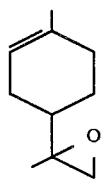

with the alkali metal thiocyanate defined according to the structure:

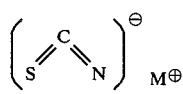

the mole ratio of alkali metal thiocyanate:epoxide may vary from about 8:1 down to about 1:1 with a preferred mole ratio of alkali metal thiocyanate:epoxide being about 4:1. The reaction takes place in a two phase system witn the alkali metal thiocyanate being dissolved in water (e.g. between a 10% and 50% solution of alkali metal thiocyanate in water). Necessarily, the reaction takes place in the presence of a phase transfer agent such as Aliquat®336 manufactured by the Henkle Chemical Company of Minneapolis, Minn. Aliquat®336 is tricapryl methyl ammonium chloride.

Thus, one aspect of our invention involving the process covered by the reaction:

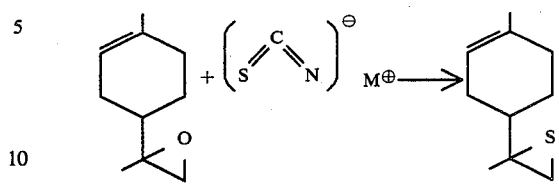

comprises the step of placing the reactants of the process in two immiscible phases, an organic phase and an aqueous alkali metal thiocyanate phase and adding to this two-phase system a "phase transfer agent" which may be one or more of several organic quaternary ammonium salts as mentioned supra.

Specific examples of phase transfer agents useful in our invention are as follows:
  tricapryl methyl ammonium chloride;
  cetyl trimethyl ammonium chloride;
  cetyl trimethyl ammonium bromide; and
  benzyl trimethyl ammonium hydroxide.

In general, the phase transfer agents most preferred have the generic formula:

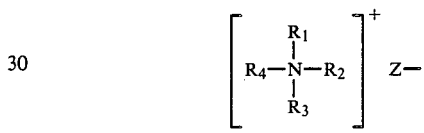

wherein at least one of $R_1$, $R_2$, $R_3$ and $R_4$ is $C_6$–$C_{14}$ aryl, $C_6$–$C_{10}$ aralkyl, $C_6$–$C_{20}$ alkyl, $C_6$–$C_{14}$ alkaryl and $C_6$–$C_{20}$ alkenyl and the other of $R_2$, $R_3$ and $R_4$ is alkyl such as methyl, ethyl, n-propyl, i-propyl, 1-butyl, 2-butyl, 1-methyl-2-propyl, 1-pentyl and 1-octyl and Z- is an anion such as chloride, bromide and hydroxide.

The reaction temperature may vary between about 45° C. and 85° C. and the pressure may vary from 1 atmosphere up to 10 atmospheres with a preferred reaction temperature being between 55° and 85° C. and a preferred and convenient reaction pressure being 1 atmosphere. At the end of the reaction, the reaction mass is separated and the organic phase is extracted with an inert extraction material, e.g. diethylether. The extract is evaporated and the resulting extract is then further reacted with a reducing agent such as lithium aluminum hydride followed by reaction with aqueous mineral acid according to the reaction sequence:

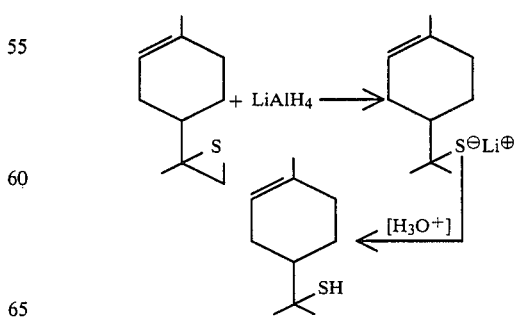

and using conditions as specified in European Published Patent Application No. 54,847 published on June 30, 1982, the specification for which is incorporated herein by reference. The reaction sequence:

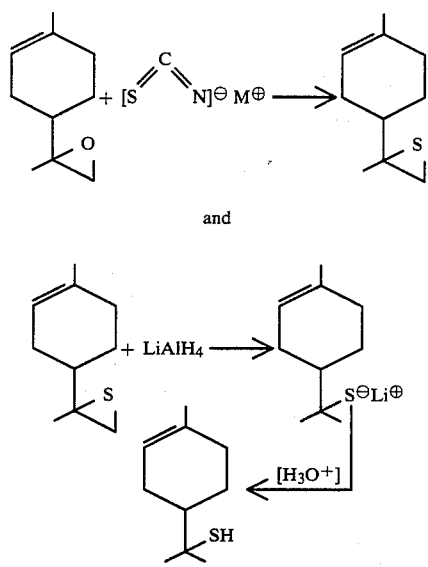

is exemplified herein in Examples I and II infra.

When the mixtures of mercapto terpenes and one or more of the oxohydrocarbon derivatives of our invention are used as food flavor adjuvants, the nature of the co-ingredients included with said mixture of mercapto terpenes and oxohydrocarbon derivatives in formulating the product composition will also serve to alter, modify, augment or enhance the organoleptic characteristics of the ultimate foodstuff, chewing gum, toothpaste, medicinal product or chewing tobacco treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without modification of the quality thereof. Thus "enhancement" of a flavor or aroma means that the enhancement agent does not add any additional flavor nuance.

As used herein, the term "foodstuff" includes both solid and liquid ingestible materials which usually do but need not have nutritional value. Thus, foodstuffs include soups, convenience foods, beverages, dairy products, candies, vegetables, cereals, soft drinks, snacks and the like.

As used herein, the term "medicinal product" includes both solids and liquids which are ingestible, non-toxic materials which have medicinal value such as cough syrups, cough drops, aspirin and chewable medicinal tablets.

The term "chewing gum" is intended to mean a composition which comprises a substantially water insoluble chewable plastic gum base such as chicle, or substitutes therefor, including julutong, guttakay, rubber or certain comestible natural or synthetic resins or waxes. Incorporated with the gum base in admixture therewith may be plasticizers or softening agents, e.g. glycerine, and a flavoring composition which incorporates the mixture of mercapto terpenes and one or more of the oxohydrocarbon derivatives of our invention and, in addition, sweetening agents which may be sugars including sucrose, dextrose and/or artificial sweeteners such as cyclamates or saccharin. Other optional ingredients may also be present.

Substances suitable for use herein as co-ingredients or flavor adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising, broadly, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxy anisole), butylated hydroxytoluene(2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates; starches, pectins, and emulsifiers, e.g., mono- and diglycerides of fatty acids, skim milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like, firming agents such as aluminum sodium sulfate, calcium chloride and calcium gluconate; texturizers, anticaking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alphamethylbutyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methylbutanal, beta,-beta-dimethyl acrolein, methyl n-amyl ketone, n-hexanal, 2-hexenal, isopentanal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, beta-damascone, alpha-damascone, beta-damascenone, acetophenone, 2-heptanone, o-hydroxy-acetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methylfurfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpinhydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl carpylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate, and terpenyl acetate; hydrocarbons such as dimethyl naphthalene, dodecane, methyldiphenyl, methyl naphthalene, myrcene, naphthalene, octadecane, tetradecane, tetramethylnaphthalene, tridecane, trimethylnaphthalene, undecane, caryophyllene, alphaphellandrene, beta-phellandrene, p-cymene 1-alpha-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essential oil, safran oil, Bulgarian rose, capsicum, yara yara and vanilla; lactones such as γ-nonalactone; sulfides, e.g., methyl sulfide and other materials such as maltol, and acetals (e.g., 1,1-diethoxyethane, 1,1-dimethyloxyethane and dimethoxymethane), piperine, chavicine, and piperidine.

The specific flavoring adjuvant selected for use may be either solid or liquid depending upon the desired physical form of the ultimate product, i.e., foodstuff, whether simulated or natural, and should, in any event, (i) be organically compatible with each of the components of the mercapto terpene-oxohydrocarbon derivative of our invention by not covering or spoiling the organoleptic properties (aroma and/or taste) thereof; (ii) be non-reactive with each of the individual components of the mercapto terpene-oxohydrocarbon derivative mixture of our invention and (iii) be capable of providing an environment in which the mercapto terpenes and the oxohydrocarbon derivatives of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of mercapto terpene-oxohydrocarbon derivative mixture employed in a particular instance can vary over a relatively wide range, depending upon the desired organoleptic effects to be achieved. Thus, correspondingly greater amounts would be necessary in those instances wherein the ultimate food composition to be flavored (e.g. with a tropical fruit flavor or with a grapefruit flavor) is relatively bland to the taste, whereas relatively minor quantities (extremely low . . . $1\times10^{-7}\%$) may suffice for purposes of enhancing the composition merely deficient in natural flavor or aroma. The primary requirement is that the amount selected be effective, i.e. sufficient to alter, modify or enhance the organoleptic characteristics of the parent composition, whether foodstuff per se, chewing gum per se, medicinal product per se, toothpaste per se, or flavoring composition itself.

The use of insufficient quantities of mixture of mercapto terpene and oxohydrocarbon derivative will, of course, substantially vitiate any possibility of obtaining the desired results, while excess quantities prove needlessly costly and in extreme cases may disrupt the flavor-aroma balance thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of mixture of mercapto terpenes and oxohydrocarbon derivatives ranging from a small but effective amount, e.g. $1\times10^{-5}$ parts per million up to about 500 parts per million based on total composition are suitable. Concentrations in excess of the maximum quantity stated are not normally recommended since they fail to provide commensurate enhancement of organoleptic properties. In those instances wherein the mixtures of mercapto terpenes and oxohydrocarbon derivatives are added to the foodstuff as an integral component of a flavoring composition, it is, of course, essential that the total quantity of flavoring composition employed be sufficient to yield an effective mercapto terpene-oxohydrocarbon derivative concentration in the foodstuff product.

Food flavoring compositions prepared in accordance with the present invention preferably contain the mixture of mercapto terpenes and oxohydrocarbon derivatives in concentrations ranging from about $1\times10^{-5}\%$ up to about 3% by weight based on the total weight of said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the mercapto terpene-oxohydrocarbon derivative mixtures with, for example, gum arabic, gum tragacanth, carrageenan gum and the like, and thereafter spray-drying the resultant mixture whereby to obtain the particulate solid product. Pre-pepared flavor mixes in powder form, e.g. a fruit flavored powder mix, are obtained by mixing the dried solid components, e.g. starch, sugar and the like, and the mixtures of mercapto terpenes and oxohydrocarbon derivatives in a dry blender until the requisite degree of uniformity is achieved.

It is presently preferred to combine the mercapto terpene-oxohydrocarbon derivatives of our invention with the following adjuvants:
maltol;
vanillin;
ethyl vanillin;
anisaldehyde;
heliotropin;
2-methyl-2-pentenoic acid;
2-methyl-2-thiopentenoic acid methyl ester;
the ethyl ester of 3-methyl-2-pentenoic acid;
the isobutyl ester of 2-methyl-3-pentenoic acid;
the ethyl ester of 2-methyl-4-pentenoic acid;
the ethyl ester of 2-methyl-3,4-pentadienoic acid;
mango extract;
mango nectar;
guava nectar;
normethyl jasmonate;
methyl dihydro jasmonate;
cis-jasmone;
p-hydroxybenzyl acetone;
geraniol;
cassia oil;
acetaldehyde;
ethyl methyl phenyl glycidate;
benzyl acetate;
dimethyl sulfide;
eugenol;
caryophyllene;
methyl cinnamate;
guiacol;
ethyl pelargonate;
cinnamaldehyde;
methyl anthranilate;
5-methyl furfural;
isoamyl acetate;
isobutyl acetate;
cuminaldehyde;
alpha ionone;
cinnamyl formate;
ethyl butyrate;
methyl cinnamate;
acetic acid;
gamma-undecalactone;
naphthyl ethyl ether;
diacetyl;
furfural;
ethyl acetate;
anethole;
2,3-dimethyl pyrazine;
2-ethyl-3-methyl pyrazine;
3-phenyl-4-pentenal;
2-phenyl-2-hexenal;
2-phenyl-2-pentenal;
3-phenyl-4-pentenal diethyl acetal;
damascone(1-crotonyl-2,2,6-trimethylcyclohex-1-one);
damascenone(1-crotonyl-2,2,6-trimethylcyclohexa-1,5-diene);
beta-cyclohomocitral(2,2,6-trimethyl-cyclohex-1-ene carboxaldehyde);
isoamyl butyrate;
cis-3-hexenol-1;
elemecine(4-allyl-1,2,6-trimethoxy benzene);
isoelemecine(4-propenyl-1,2,6-trimethoxy benzene)
2-(4-hydroxy-4-methylpentyl)norbornadiene prepared according to U.S. Pat. No. 3,886,289 issued on May 27, 1975.

It will thus be apparent that the mixture of mercapto terpenes and oxohydrocarbon derivatives of our invention can be utilized to alter, modify, augment or enhance sensory properties, particularly organoleptic properties such as flavors and/or fragrances of a wide variety of consumable materials.

The following Examples I and II serve to illustrate a method for preparing one of the components of the mixtures of our invention. The following Examples III et seq. serve to illustrate the organoleptic utilities of products of our invention and our invention itself. This invention is to be considered restricted to the examples only as indicated in the appended claims.

All parts and percentages given herein are by weight unless otherwise specified.

EXAMPLE I

PREPARATION OF LIMONENE THIIRANE

Reaction:

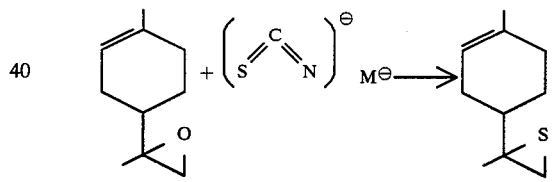

wherein M represents sodium.

Into a 100 ml 3-neck reaction flask equipped with magnetic stirrer, thermometer, reflux condenser and heating mantle is placed 10.7 grams of sodium thiocyanate (0.132 moles) and 19.2 grams of water. The sodium thiocyanate and water mixture is stirred in order to dissolve the sodium thiocyanate. To the sodium thiocyanate solution is added 5.0 grams of limonene epoxide (0.033 moles) and 10 drops (0.10 grams) of Aliquat®336.

While maintaining the reaction mass at 22° C., a mixture of 5.0 grams of limonene epoxide (0.033 moles) and 10 drops (0.10 grams) of Aliquat®336 (tricapryl methyl ammonium chloride manufactured by the Henkle Chemical Company of Minneapolis, Minn.) is added. The reaction mass is then heated to 60°-85° C. and maintained at a temperature of 80°-85° C. for a period of 30 hours.

At the end of the 30 hour period, the reaction mass is split into two phases; an aqueous phase and an organic phase. The aqueous phase is extracted with 10 ml of diethylether and combined with the organic phase. The organic phase is washed with two 10 ml portions of water and dried over anhydrous sodium sulfate. The resulting product is then stripped of solvent and utilized for Example II.

FIG. 1 is the GLC profile for the resulting reaction product of Example I containing the compound having the structure:

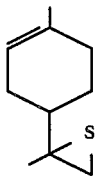

(conditions: Carbowax column programmed at 120°-210° C. at 8° C. per minute). The peak indicated by reference numeral "10" is the peak for the compound having the structure:

EXAMPLE II

PREPARATION OF MIXTURE OF α-TERPINEOL AND 1-p-MENTHENE-8-THIOL

Reaction:

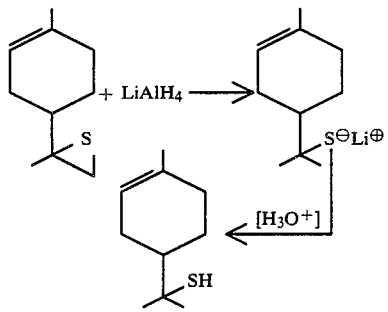

Into a 100 ml 3-neck flask equipped with magnetic stirrer, thermometer, reflux condenser, addition funnel and nitrogen blanket apparatus is placed 1.02 grams (0.0268 moles) of lithium aluminum hydride dissolved in 10 ml tetrahydrofuran. The resulting mixture is maintained at a temperature of 25°-30° C. with stirring. Over a period of 10 minutes, 4.5 grams of the thiirane of limonene (0.0268 moles) having the structure:

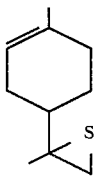

produced according to Example I is added to the reaction mass. The reaction mass is then stirred at 30°-36° C. for a period of 1 hour.

10 ml water is then slowly added to the reaction mass followed by 13 ml 10% sulfuric acid followed by 15 ml water and then 5 ml 10% sulfuric acid and then 10 ml water.

The aqueous phase is extracted with one 10 ml portion of n-pentane. The organic phase is washed with three 20 ml portions of water. The organic phases are combined and dried over anhydrous sodium sulfate.

The resulting product after being stripped of solvent is distilled on a 15" stone packed column yielding the following fractions:

| Fraction Number | Vapor Temp. (°C.) | Liquid Temp. (°C.) | Vacuum mm/Hg | Weight of Fraction (grams) |
|---|---|---|---|---|
| 1 | 45/47 | 52/53.5 | 0.33 | 0.2 |
| 2 | 51 | 57.5 | 0.33 | 0.6 |
| 3 | 58 | 60.5 | 0.33 | 1.2 |
| 4 | 60/58 | 84 | 0.35 | 0.2 |

Fractions 1-4 are bulked. Bulked fractions 1-4 have a GLC profile as illustrated in FIG. 2. Bulked fractions 1-4 consist essentially of the compound defined according to the structure:

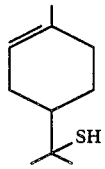

The resulting product is a mixture of the compound having the structure:

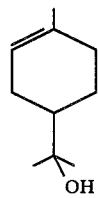

and a racemic mixture of the isomers of the compound having the structure:

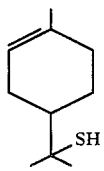

At the rate of 1-5 ppm, this compound is added to β-phenylethyl alcohol. The resulting material has an interesting natural rose petal, green, iris-like and hyacinth aroma.

At $1 \times 10^{-5}$ ppm, the resulting material has a raspberry/guava, grapefruit-like, black current-like, tomato leaf and passion fruit aroma and taste profile causing it to be useful in tomato, guava, grapefruit, tropical fruit, raspberry, strawberry and passion fruit flavors and flavored foodstuffs.

EXAMPLE III

RASPBERRY/TROPICAL FRUIT FLAVOR FORMULATION

The following basic raspberry flavor formulation is produced:

| Ingredient | Parts by Weight |
| --- | --- |
| Vanillin | 2.0 |
| Maltol | 5.0 |
| Parahydroxybenzylacetone | 5.0 |
| Alpha-ionone (10% is propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |

At the rate of $10^{-2}$ ppm, the mixture produced according to Example II containing the compounds having the structures:

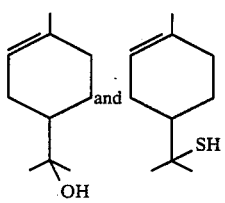

is added to half of the above formulation. The formulation with the mixture of t-mercapto terpene and α-terpineol prepared according to Example II is compared to the formula without the t-mercapto terpene and α-terpineol at the rate of 0.01% (100 ppm) in water and evaluated by a bench panel of 5 individuals not employed by the assignee of the instant application and independent of the inventors in this case.

The flavor containing the mixture of compounds having the structures:

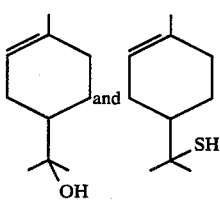

is found to have substantially sweeter aroma notes with tropical fruit nuances and a profile which can be described as raspberry/guava, grapefruit, black current, tomato leaf and passion fruit. It is the unanimous opinion of the bench panel that the mixture of compounds having the structures:

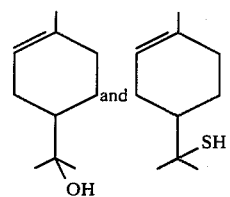

causes the original raspberry flavor to have a very fresh tropical fruit-like aroma and taste profile in combination with a raspberry/guava aroma and taste. Overall natural raspberry/guava aroma and taste is substantially reproduced by this formulation. The formulation is preferred unanimously over the formulation without the mixture of compounds having the structures:

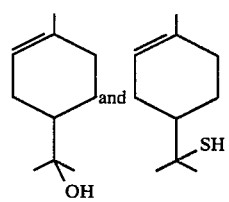

EXAMPLE IV

A. Powder Flavor Composition 20 grams of the flavor composition of Example III is emulsified in a solution containing 300 gm gum acacia and 700 gm water. The emulsion is spray-dried with a Bowen Lab Model Drier utilizing 260 c.f.m. of air with an inlet temperature of 500° F., an outlet temperature of 200° F. and a wheel speed of 50,000 r.p.m.

B. Sustained Release Flavor

The following mixture is prepared:

| Ingredient | Parts by Weight |
| --- | --- |
| Liquid raspberry/guava flavor composition of Example III | 20 |
| Propylene glycol | 9 |
| Cab-O-Sil ® M-5 (Brand of silica produced by the Cabot Corporation of 125 High St., Boston, Mass. 02110, Physical properties: Surface area: 200 m²/gm Nominal particle size: 0.012 microns Density: 2.3 lbs/cu. ft.) | 5 |

The Cab-O-Sil ® is dispersed in the liquid raspberry flavor composition of Example III with vigorous stirring, thereby resulting in a viscous liquid. 71 parts by weight of the powder flavor composition of Part A, supra, is then blended into the said viscous liquid, with stirring, at 25° C. for a period of 30 minutes resulting in a dry, free-flowing sustained release flavor powder.

EXAMPLE V

Ten parts by weight of 50 Bloom pigskin gelatin is added to 90 parts by weight of water at a temperature of 150° F. The mixture is agitated until the gelatin is completely dissolved and the solution is cooled to 120° F. Twenty parts by weight of the liquid flavor composition of Example III is added to the solution which is then homogenized to form an emulsion having a particle size typically in the range of 5–40 microns. This material is kept at 120° F. under which conditions the gelatin will not jell.

Coacervation is induced by adding, slowly and uniformly, forty parts by weight of a 20% aqueous solution of sodium sulphate. During coacervation, the gelatin molecules are deposited uniformly about each oil droplet as a nucleus.

Gelatin is effected by pouring the heated coacervate mixture into 1,000 parts by weight of 7% aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE VI

One hundred parts by weight of chicle are mixed with four parts by weight of the flavor prepared in accordance with Example IV. Three hundred parts of sucrose and one hundred parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting raspberry/guava flavor.

EXAMPLE VII

CHEWING GUM

One hundred parts by weight of chicle are mixed with eighteen parts by weight of the flavor prepared in accordance with Example V. Three hundred parts of sucrose and one hundred parts of corn syrup are then added. Mixing is effected in a ribbon blender with jacketed side walls of the type manufactured by the Baker Perkins Co.

The resultant chewing gum is then manufactured into strips 1 inch in width and 0.1 inches in thickness. The strips are cut into lengths of 3 inches each. On chewing, the chewing gum has a pleasant long lasting raspberry/guava flavor

EXAMPLE VIII

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled water |
| .100 | Sodium benzoate |
| .125 | Saccharin sodium |
| .400 | Stannous fluoride |
| Group "B" | |
| 12.500 | Calcium carbonate |
| 37.200 | Dicalcium phosphate (dihydrate) |
| Group "C" | |
| 2.000 | Sodium n-lauroyl sarcosinate (foaming agent) |
| Group "D" | |
| 1.200 | Flavor material of Example IV |
| 100.000 (total) | |

Procedure:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized and finally tubed.

The resulting toothpaste when used in a normal toothbrushing procedure yields a pleasant raspberry/guava flavor of constant strong intensity throughout said procedure (1–1.5 minutes).

EXAMPLE IX

CHEWABLE VITAMIN TABLETS

The flavor material produced according to the process of Example V is added to a chewable vitamin tablet formulation at a rate of 10 gm/kg which chewable vitamin tablet formulation is prepared as follows:

In a Hobart Mixer, the following materials are blended to homogeneity:

| | Gms/1000 tablets |
|---|---|
| Vitamin C (ascorbic acid) as ascorbic acid-sodium ascorbate mixture 1:1 | 70.0 |
| Vitamin $B_1$ (thiamine mononitrate) as Rocoat ® thiamine mononitrate 33⅓% (Hoffman LaRoche) | 4.0 |
| Vitamin $B_2$ (riboflavin) as Rocoat ® riboflavin 33⅓% | 5.0 |
| Vitamin $B_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-biotin | 0.044 |
| Certified lake color | 5.0 |
| Flavor of Example V | as indicated above |
| Sweetener - sodium saccharin | 1.0 |
| Magnesium stearate lubricant | 10.0 |
| Mannitol q.s. to make | 500.0 |

Preliminary tablets are prepared by slugging with flatfaced punches and grinding the slugs to 14 mesh. 13.5 grams dry vitamin A acetate and 0.6 grams vitamin D are then added as beadlets. The entire blend is then compressed using concave punches at 0.5 grams each.

Chewing of the resultant tablets yields a pleasant, long-lasting, consistently strong raspberry/guava flavor (with raspberry and tropical fruit nuances) for a period of 12 minutes.

EXAMPLE X

ROSE FORMULATION

The following mixture is prepared:

| Ingredients | Parts by Weight |
|---|---|
| Rhodinol | 270.0 |
| Nerol | 90.0 |
| Linalool | 30.0 |
| Terpineol | 30.0 |
| Phenyl Ethyl Alcohol | 12.0 |
| Terpinenol | 5.0 |
| Linalyl acetate | 1.5 |
| Citronellyl acetate | 15.0 |
| Geranyl acetate | 10.0 |
| Eugenol | 33.0 |
| Citral | 15.0 |
| Phenyl Ethyl Acetate | 20.0 |
| Rose oxide | 8.0 |
| Guaiacol | 30.0 |
| l-citronellal | 90.0 |
| Neryl acetate | 3.0 |
| Clove bud oil | 1.0 |
| Cadinene | 2.0 |
| Guaiene | 1.0 |
| Gum turpentine | 12.0 |
| Alpha-pinene | 1.0 |
| Myrcene | 5.0 |
| Limonene | 2.0 |
| p-cymene | 1.0 |

To the foregoing formulation 0.003 parts by weight of the mixture of compounds having the structures:

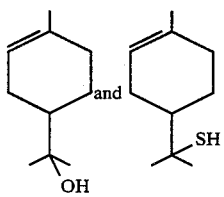

produced according to Example II and 30 parts by weight of 0.1 solution of 3-methyl-1-phenyl-pentanol-5 in diethyl phthalate and 15 parts by weight of a 0.1% solution of beta-damascenone in diethyl phthalate is added.

The resultant mixture has a rose petal topnote with hyacinth, iris and green nuances and is preferred by a bench panel of 4 members (independent of the inventors and the assignee of the instant application). The bench panel unanimously agrees that the resulting fragrance formulation has a much more "sophisticated" rose petal aroma and much more natural-like rose aroma than any rose aromas known in the art. Indeed, a similar effect is achieved without the use of the 3-methyl-1-phenyl-pentanol-5 and/or the beta-damascenone. A somewhat enhanced effect with a brighter rose topnote is added when using trans,trans-delta-damascone in place of the beta-damascenone.

EXAMPLE XI

PREPARATION OF A SOAP COMPOSITION

One hundred grams of soap chips are prepared according to Example V of U.S. Pat. No. 4,058,490 issued on Nov. 15, 1977 as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is drum dried. The resulting solid actives are then blended in a chip mixer with 10 lbs. water, 0.2 lbs. titanium hydroxide"

and mixed with one gram of the perfume composition of Example X until a substantially homogeneous composition is obtained. The perfumed soap composition manifests an excellent rose character with rose petal, green, hyacinth and iris nuances.

EXAMPLE XII

PREPARATION OF A DETERGENT COMPOSITION

A total of 100 grams of detergent powder prepared according to U.S. Pat. No. 4,058,472 and containing 5% by weight of the sodium salts of a mixture of sulfonated $C_{14}$-$C_{18}$ alkyl catechol as a surface active component, the mixture being 60 parts by weight of mono-$C_{14}$-$C_{18}$ alkyl catechol, 35% sodium tetrapyrrole phosphate, 30% of sodium carboxymethylcellulose and 7% of starch is mixed with 0.15 grams of the perfume composition of Example X until a substantially homogeneous composition is obtained. This composition has an excellent rose petal aroma with green, hyacinth-like and iris nuances.

EXAMPLE XIII

PERFUMED LIQUID DETERGENT

Concentrated liquid detergents each with rose petal, hyacinth and iris aromas and green undertones are prepared containing 0.10%, 0.15%, 0.20% and 0.25% of a mixture of compounds having the structures:

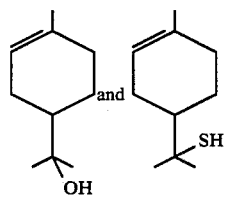

(which mixture is prepared according to Example II) in an amount of 0.001% and, in addition, a mixture of beta-damascenone and 3-methyl-1-phenyl-pentanol-5 (the beta-damascenone and 3-methyl-1-phenyl-pentanol-5 being in a weight ratio of 1:0.1). They are prepared by adding and homogeneously mixing the appropriate quantity of mixture of compounds having the structures:

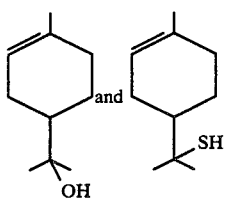

together with the beta-damascenone and 3-methyl-1-phenyl-pentanol-5 in the liquid detergent. The detergents all possess rose petal aromas with iris, hyacinth-like and green undertones, the intensity increasing with greater concentrations of mixture of compounds having the structures:

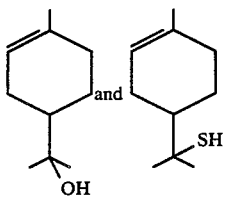

beta-damascenone and 3-methyl-1-phenyl-pentanol-5.

EXAMPLE XIV

PREPARATION OF COLOGNE AND HANDKERCHIEF PERFUME

The composition of Example X is incorporated in colognes at concentrations of 1.5%, 2.0%, 2.5%, 3.0% and 3.5% in 75%, 80%, 85% and 90% aqueous ethanol; and into handkerchief perfumes at concentrations of 15%, 20% and 25% (in 85%, 90% and 95% aqueous ethanol). The use of the compounds having the structures:

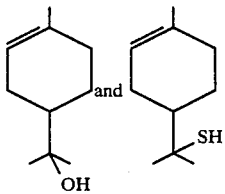

produced according to Example II taken alone or taken further together with beta-damascenone and 3-methyl-1-phenyl-pentanol-5 in the composition of Example X affords a distinct and definite strong rose petal aroma with hyacinth-like, iris-like and green undertones to the handkerchief perfume and to the cologne.

EXAMPLE XV

Utilizing the procedure of Example I on column 15 of U.S. Pat. No. 3,632,396 (the specification of which is incorporated by reference herein), a nonwoven cloth substrate useful as a drier-added fabric softening article of manufacture is prepared wherein the substrate, the substrate coating and the outer coating and the perfuming material are as follows:
1. a water "dissolvable" paper ("Dissolvo Paper");
2. Adogen 448 (m.p. about 140° F.) as the substrate coating; and
3. an outer coating having the following formulation (m.p. about 150° F.):
   57% $C_{20-22}$ HAPS
   22% isopropyl alcohol
   20% antistatic agent
   1% of a mixture of 0.003% of the mixture produced according to Example II containing the compounds having the structures:

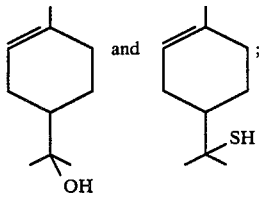

1% 3-methyl-1-phenyl-pentanol-5 and 0.1% of trans,trans-delta damascone giving rise to a rose petal, hyacinth, iris and green aroma profile.

Fabric softening compositions prepared as set forth above having the above aroma characteristics essentially consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The resulting aroma being described as rose petal, hyacinth, green and iris-like is imparted to the head space in the drier on operation thereof using the said drier-added fabric softening nonwoven fabric.

EXAMPLE XVI

Scented polyethylene pellets having a pronounced rose petal, green, hyacinth and iris scent are prepared as follows:

Seventy-five founds of polyethylene of a melting point of about 220° F. are heated to about 230° F. in a container of the kind illustrated in FIGS. 3 and 4. Twenty-five pounds of the perfume material of Example III is then added quickly to the liquified polyethylene. The lid 228 is put in place and the agitating means 273 are actuated. The temperature is maintained at about 225° F. and the mixing is then continued for about 5-15 minutes. The valve 230 is then opened to allow flow of the molten polyethylene enriched with the perfume composition of Example III-containing material to exit through the orifices 234. The liquid falling through the orifices 234 solidifies almost instantaneously upon impact with the moving, cooled conveyor 238. Solid polyethylene beads or pellets 244 having an aroma which can be described as rose petal, green, hyacinth-like and iris-like are then formed. Analysis demonstrates that the pellets contain about 25% of the perfume composition of Example III so that almost no losses of the scenting substance occur. These pellets may be called master pellets.

Fifty pounds of the scent-containing master pellets are then added to 1,000 pounds of unscented polyethylene powder and the mass is heated to the liquid state. The liquid is molded into thin sheets or films. The sheets or films have a pronounced rose petal, hyacinth, iris-like and green aroma. The sheets are then also fabricated into garbage bags which have such an aroma.

EXAMPLE XVII

MANGO NECTAR

Goya ® mango nectar manufactured by Goya Products, Inc. of New York is intimately admixed with the mixture of Example II containing the compounds having the structures:

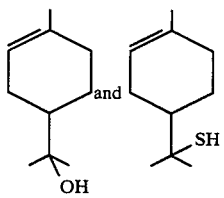

at a rate of $10^{-4}$ ppm. The mango nectar has an enhanced "natural-like", delicate taste and is preferred by a bench panel of 4 independent members (independent of assignee and inventors) to the mango nectar without such mixture. When 0.01% of 1-methyl-3-n-propyl-2,4-oxathiane is added to the mango nectar already containing the compounds having the structures:

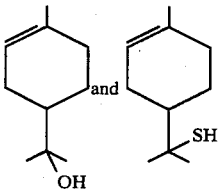

a slight improvement occurs. Overall, the mango nectar can be described as "natural mango with faint but aesthetically pleasing raspberry/guava, grapefruit and black current nuances".

What is claimed is:

1. A process for preparing a composition of matter including as a major proportion the compound defined according to the structure:

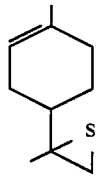

comprising the step of reacting the compound having the structure:

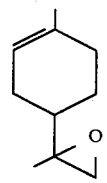

with an alkali metal thiocyanate having the structure:

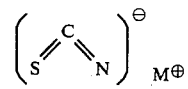

according to the reaction:

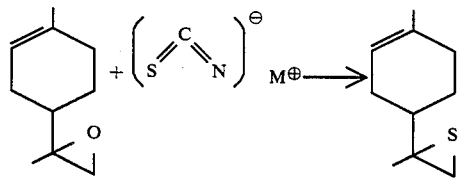

wherein M represents alkali metal in the presence of a phase transfer catalyst, said phase transfer catalyst having the general formula:

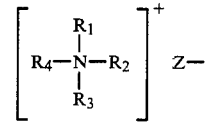

wherein at least one of $R_1$, $R_2$, $R_3$ and $R_4$ is $C_6$-$C_{14}$ aryl, $C_6$-$C_{10}$ aralkyl, $C_6$-$C_{20}$ alkyl, $C_6$-$C_{14}$ alkaryl and $C_6$-$C_{20}$ alkenyl and the other of $R_2$, $R_3$ and $R_4$ is alkyl selected from the group consisting of methyl, ethyl, n-propyl, i-propyl, 1-butyl, 2-butyl, 1-methyl-2-propyl, 1-pentyl and 1-octyl and $Z^-$ is an anion selected from the group consisting of chloride, bromide and hydroxide, the reaction temperature varying from about 45° C. up to about 85° C.; the pressure of reaction varying from one atmosphere up to 10 atmospheres; the mole ratio of alkali metal thiocyanate:epoxide varying from about 8:1 down to about 1:1; the said alkali metal thiocyanate being dissolved in water with the alkali metal thiocyanate being in a concentration of between 10% and 50% in said water.

* * * * *